United States Patent [19]

Watson et al.

[11] Patent Number: 5,912,168
[45] Date of Patent: Jun. 15, 1999

[54] CD95 REGULATORY GENE SEQUENCES

[75] Inventors: James D. Watson; Fritz Rudert, both of Auckland, New Zealand

[73] Assignee: Genesis Research & Development Corporation Limited, Auckland, New Zealand

[21] Appl. No.: 08/713,557

[22] Filed: Aug. 30, 1996

[51] Int. Cl.$^6$ ............................ C12N 15/63; C12N 15/11; C12N 15/12

[52] U.S. Cl. .................... 435/320.1; 536/23.1; 536/23.5; 536/24.1

[58] Field of Search ........................ 435/320.1; 536/23.1, 536/23.5, 24.1

[56] References Cited

U.S. PATENT DOCUMENTS

| | | | |
|---|---|---|---|
| 5,399,586 | 3/1995 | Davies et al. | 514/448 |
| 5,464,833 | 11/1995 | Nakai et al. | 514/251 |
| 5,500,432 | 3/1996 | Nicolaou et al. | 514/281 |

FOREIGN PATENT DOCUMENTS

| | | |
|---|---|---|
| 8902472 | 3/1989 | WIPO . |
| 9207072 | 4/1992 | WIPO . |
| 9304203 | 4/1993 | WIPO . |
| 9502053 | 1/1995 | WIPO . |
| 9508554 | 3/1995 | WIPO . |
| 9500642 | 5/1995 | WIPO . |

OTHER PUBLICATIONS

Fritz Rudert et al., Identification of a Silencer, Enhancer, and Basal Promoter Region in the Human CD95 (fas/APO–1) Gene, *Gene, DNA and Cell Biology 14*:11, pp. 931–037, 1995.

D.L. Vaux et al., The molecular biology of apoptosis, *Porc. Natl. Acad. Sci. USA 93*, pp. 2239–2244, Mar. 1996.

Abdallah Fanidi et al., Applications of apoptosis: making death pay, *Tibtech 12*, pp. 219–221, Jun. 1994.

Jean Claude Ameisen, Programmed cell death and AIDS: from hypothesis to experiment, *Immunology Today 13*:10, pp. 388–391, 1992.

Gene Bylinsky, Cell Suicide: The Birth of A Mega–Market, *Fortune Magazine,* May, 15, 1995.

Philip L. Cohen et al., The lpr and gld genes in systemic autoimmunity: life and death in the Fas lane, *Immunolgy Today 13*:11, pp. 427–428, 1992.

Erhard Hofer et al., Candidate natural killer receptors, *Immunology Today 13*:11, pp. 429–430, 1992.

Jean Claude Ameisen et al., The relevance of apoptosis to AIDS pathogenesis, *Trends in Cell Biology 5*, pp. 27–32, Jan. 5, 1995.

David H. Lynch et al., Fas and FasL in the homeostatic regulation of immune responses, *Immunology Today 16*:12, pp. 569–574, 1995.

Wada et al., Transcription Stimulation of the Fas–encoding Gene by Nuclear Factor for Interleukin–6 Expression upon Influenza Virus Infection, *Jour. of Biological Chemistry 370*:30, pp. 18007–12, 1995.

Behrmann et al., Structure of the human APO–1 gene, *Eur. J. Immunol. 24*: pp. 3057–3062, 1994.

Jianhua Cheng et al., Characterization of Human Fas Gene, *Journal of Immunology 154*, pp. 1239–1245, 1995.

Nancy C. Andrews et al., a Rapid micropreparation technique for extraction of DNA–binding proteins from limiting numbers of mammalian cells, *Nucleic Acids research 19*:9, p. 2499, 1991.

Shigeki Miyamoto et al., Ultraviolet Cross–Linking of DNA Binding Proteins, *Methods of Enzymology 254*, pp. 632–641, 1995.

Min Li et al., *Appendix I*—(Southewestern Protocol), pp. 186–196, 1991.

Abul K. Abbas, Die and Let Live: Eliminating Dangerous Lymphocytes, *Cell 84*, pp. 655–657, Mar. 8, 1996.

Leanne S. Coles et al., A sequence–specific single–strand DNA binding protein that contacts repressor sequences in the human GM–CSF promoter, *Nucleic Acids Research 22*:20, pp. 42764283, 1994.

LiFeng Good et al., Activation of the IL–2 gene promoter by HTLV–1 Tax involves induction of NF–AT complexes bound to the CD28–responsive element, *EMBO Jounal 15*:14, pp. 3744–3750, 1996.

Fay Jenkins et al., Multiple Signals are Required for Function of the Human Granulocyte–Macrophage Colony Stimulating Factor Gene Promoter in T Cells, *Journal of Immunology*, pp. 1240–1251, 1995.

*Primary Examiner*—Terry McKelvey
*Attorney, Agent, or Firm*—Ann W. Speckman; Janet Sleath

[57] ABSTRACT

Regulatory DNA sequences that silence and enhance transcription of coding portions of the CD95 gene, which is instrumental in apoptosis, are disclosed. Proteinaceous transcription factors that bind to the silencer and enhancer regulatory sequences are also disclosed and are useful for modulating the expression of CD95 or other proteins. Methods for regulating apoptosis have therapeutic and prophylactic applications for a variety of disorders, including cancer, viral and retroviral infections, neurodegenerative disorders, immune system dysfunction, and other disorders.

10 Claims, 10 Drawing Sheets

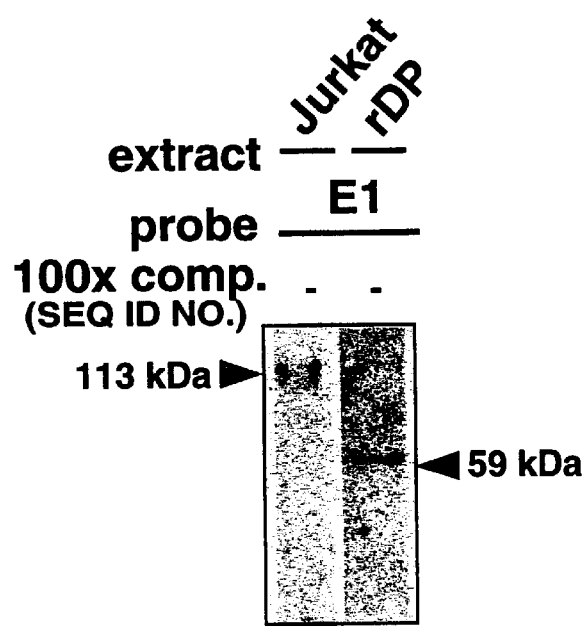
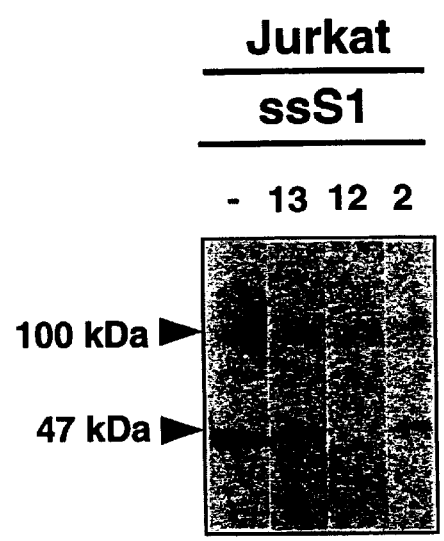
Fig. 8A
Fig. 8B

CD95 REGULATORY GENE SEQUENCES

FIELD OF THE INVENTION

The present invention relates, generally, to regulation of expression of a gene encoding the CD95 receptor, which plays an important role in apoptosis, or programmed cell death. More specifically, the present invention relates to regulation of CD95 gene expression through identification of regulatory sites on the CD95 gene, proteinaceous transcription factors that bind to the CD95 regulatory sites, and methods for regulating CD95 gene transcription and expression.

BACKGROUND OF THE INVENTION

Apoptosis is a cell suicide mechanism that is used by multicellular organisms to regulate physiological cell death for purposes of defense, development, homeostasis and aging. Apoptosis is an active process modulated by its own regulatory system and genetics and is generally characterized by morphological changes including loss of contact of a cell with its neighbors, chromatin condensation, membrane blebbing, cytoplasmic condensation, DNA fragmentation and, eventually, the generation of membrane-enclosed apoptotic bodies that are phagocytosed by neighboring cells.

CD95 (also referred to as Fas or APO-1) is an important receptor in apoptosis. Apoptotic cell death is triggered by an interaction of the CD95 receptor with its ligand CD95L. CD95 is a member of the tumor necrosis factor (TNF) receptor family of cell surface proteins, and CD95L is a member of the TNF family of membrane and secreted proteins. CD95 is expressed on a wide variety of cell types, either constitutively or inducibly. CD95 is expressed, for example, on activated T and B cells, and its mRNA has been detected in other tissues including thymus, spleen, liver, ovary, lung, and heart.

CD95 has been implicated in mediating nonspecific T-cell cytotoxicity and activation-induced cell death (AICD) in the peripheral immune system. When apoptosis is induced in T cells by activation through an antigen receptor, signals are passed into the cell, leading to activation of the cell and expression of c-myc. The cell up-regulates both CD95 and CD95L and expresses them on the cell surface. These molecules then interact with each other, in an autocrine or paracrine manner, initiating the cell death-inducing signaling pathway. Overexpression of CD95 receptor signaling domain results in apoptosis and cell death.

Regulating apoptosis has therapeutic and/or prophylactic implications for diseases where apoptosis causes the pathology, including chronic neurodegenerative disorders such as Alzheimer's and Parkinson's diseases and multiple sclerosis, and immunosuppressive disorders, both genetic and acquired. Similarly, regulating apoptosis may have therapeutic benefits under circumstances in which apoptosis occurs as a result of trauma, such as strokes and heart attacks. Agents that block apoptosis may be useful in treating ischemic conditions, such as heart attacks, strokes or reperfusion injury, by blocking the apoptotic response in cells. Pathological suppression of apoptosis appears to be an important factor in neoplastic diseases and viral infection. Apoptosis is suppressed, for example, in proliferating tumor cells. HIV/AIDS infection produces unregulated and untimely apoptosis in crucial defenders of the immune system, namely CD-4 cells. Moreover, modulation of apoptosis may increase tolerance to pharmaceutical agents such as chemotherapeutic and radiotherapeutic agents that stress but, absent an apoptotic mechanism, may not kill cells. Regulation of apoptosis may also have implications for in vitro cell growth and maintenance and may be used to produce more robust cell lines and increase production of recombinant proteins.

The numerous applications in which regulation of apoptosis may play an important role underscore the importance of developing a more complete understanding of expression of the CD95 receptor. Identification of regulatory sequences on the CD95 gene, as well as transcription factors that bind to such regulatory sequences, will provide means for modulating transcription and expression of this important receptor, thereby providing a means to regulate apoptosis.

BRIEF DESCRIPTION OF THE INVENTION

In one aspect, the present invention provides novel, isolated and purified polynucleotides that are involved in transcriptional regulation of the CD95 receptor and variants thereof which possess similar regulatory properties. Polynucleotides that play a role in enhancing and silencing transcription from the CD95 promoter are disclosed. Regulatory polynucleotides of the present invention are located in a 70 bp region about 1 kb upstream from the coding portion of the CD95 gene. A presently preferred polynucleotide that functions as a regulatory element in the enhancement of transcription from the CD95 promoter is described in SEQ ID NO:1. A presently preferred polynucleotide that functions as a regulatory element in silencing transcription from the CD95 promoter is described in SEQ ID NO:2.

In another aspect, the present invention discloses novel isolated and purified polynucleotides that provide sites for binding of transcription factors that regulate transcription from the CD95 promoter. All or a portion of the polynucleotide sequences described in SEQ ID NOS:1 and 2 provide binding sites for transcription factors that modulate transcription of coding portions of the CD95 gene. A presently preferred polynucleotide sequence consensus motif that provides a binding site for transcription factor(s) that enhance transcription from the CD95 promoter is set forth in SEQ ID NO:3. Presently preferred polynucleotides that provide sites for binding of transcription factors that enhance transcription from the CD95 promoter are set forth in SEQ ID NOS:4, 5 and 6. Presently preferred polynucleotides that provide sites for binding of a transcription factor that silences transcription from the CD95 promoter are set forth in SEQ ID NOS:2 and 7.

Yet another aspect of the present invention relates to proteinaceous binding molecules, referred to as transcription factors, that bind specifically to the CD95 silencer and enhancer regions described above to enhance or inhibit transcription of the CD95 gene. The term "CD95 transcription factor," as used herein, refers to any one of a series of proteinaceous molecules which are capable of binding to polynucleotides that regulate transcription and/or expression of CD95. CD95 transcription factors derived from human, as well as other mammalian species, and partially or wholly synthesized proteinaceous molecules are within the scope of this invention. Transcription factors that bind to polynucleotide probes corresponding to the enhancer regulatory sequences described above (SEQ ID NOS:1 and 3–6) form distinct DNA/protein complexes having molecular weights of approximately 59 kDa, 113 kDa and 200–300 kDa. Experimental evidence suggests that transcription factors capable of binding to CD95 enhancer regulatory polynucleotides exhibit double stranded binding activity. Transcription factors that bind to polynucleotide probes corresponding to all or a portion of the silencer regulatory polynucleotide sequences (SEQ ID NOS:2, 7) form distinct DNA/protein complexes having molecular weights of approximately 47 kDa, 77 kDa and 100 kDa. Experimental evidence suggests that transcription factors capable of binding to CD95 silencer regulatory polynucleotides exhibit single stranded binding activity.

Another aspect of the present invention relates to use of the regulatory polynucleotides and/or transcription factors of the present invention to modulate transcription of a gene other than CD95. Modulation of other genes may be accomplished for example, by making a DNA construct in which coding portions of selected genes are operably linked with a regulatory polynucleotide of the present invention and a suitable promoter. Appropriate transcription factors may be introduced in vitro or in vivo and play a role in modulating transcription and expression of the selected gene. Techniques for synthesizing functional DNA constructs of this type are well known.

Yet another aspect of the present invention relates to the identification of CD95 transcriptional start sites. Several such sites are identified below.

The regulatory polynucleotides and transcription factors disclosed in the present invention have numerous uses and applications. Such polynucleotides and transcription factors are useful, for example, for studying regulation of CD95 transcription, and for modulating (i.e. inhibiting, blocking or stimulating) transcription and expression of coding portions of the CD95 gene both in vitro and in vivo. Regulatory polynucleotides and transcription factors disclosed herein may also be used to modulate transcription from another gene appropriately linked to a regulatory polynucleotide and a suitable promoter. Several illustrative applications are briefly described below.

Regulatory polynucleotides and CD95 transcription factors of the present invention are useful for studying regulation of CD95 both in vitro and in vivo. For example, regulatory polynucleotides and CD95 transcription factors are useful for identifying cell types and populations having CD95 transcription enhancing and/or silencing regulatory capabilities. Numerous techniques may be employed. Using CD95 regulatory polynucleotides as probes, for example, nuclear extracts from various cell sources may be screened by electrophoretic mobility shift assay (EMSA) for the presence or absence of the respective DNA/protein complexes. Expression of transcription factors capable of binding to such probes can be directly assayed by amplifying a portion of their cDNAs, for example by polymerase chain reaction ("PCR"), or by detecting mRNA for these factors using DNA/RNA or RNA/RNA hybridization techniques, such as Northern analysis or RNase protection assays. The CD95 silencer and enhancer polynucleotides may also be used to screen for the presence and/or activity of the respective regulatory factors in a cell transfection system, wherein expression of various well established reporter genes, such as chloramphenicol acetyl transferase gene, beta galactosidase gene, firefly luciferase gene, renilla luciferase gene, or green fluorescent protein gene is detected. Identification of cell types and populations which contain CD95 regulatory factors may have significant ramifications for the development of therapeutic and prophylactic agents.

Polynucleotides of the present invention also have application for identification of modulators (positive or negative regulators) of CD95 transcription. A screening assay, for example, may utilize transiently or stably transfected reporter constructs comprising the regulatory polynucleotides of the present invention to assess CD95 transcription. As described above, the regulatory silencer and/or enhancer sequences may be fused to an appropriate promoter driving the expression of one of the above mentioned reporter genes. Such reporter constructs may be transiently transfected, e.g. by lipofection, electroporation, DEAE dextran or Ca-phosphate co-precipitation methods, into appropriate cell lines or primary cells. Reporter activity may then be measured by chemiluminescent, fluorescent, ELISA-based or enzymatic methods (radioactive or nonradioactive). Such screening assays compare favorably with assays that assess the protein turnover of the CD95 receptor.

According to another aspect of the invention, the use of eukaryotic host cells transfected with regulatory polynucleotides of the present invention that mimic the regulated, inducible transcription of the CD95 gene allows identification and testing of the potency of physiological stimulators and inhibitors of CD95 transcription.

Polynucleotides of the present invention are also useful in screening assays to identify molecules capable of binding to regulatory portions of the CD95 gene and thereby regulating transcription of the CD95 gene. Assays for identifying binding molecules using polynucleotide probes are well known in the art and include affinity purification using, for example, trapping of specific DNA/protein complexes formed with biotinylated binding sequences, to a streptavidin matrix or coupling binding site-containing polynucleotides covalently to an appropriate column matrix, such as activated agarose or sepharose. The CD95 regulatory polynucleotides may also be used to monitor specific binding activity of individual fractions of nuclear or whole cell extracts from appropriate sources after treatment by various biochemical and/or biophysical fractionation regimens. The CD95 regulatory polynucleotides may also be employed in a yeast one-hybrid functional cloning system. Regulatory polynucleotides may be cloned in a yeast shuttle vector to activate transcription of a biosynthetic marker or a survival gene which is expressed when at least the DNA binding domain of the cognate transcription factor (provided by a cDNA library and expressed in a second vector as a hybrid with the activation domain of another, suitable transcription factor) binds to this sequence. Identification, isolation and purification of such binding molecules provides a mechanism for modulating transcription of coding portions of the CD95 gene, both in vitro and in vivo.

Similarly, CD95 transcription factors of the present invention are useful for identification and purification of functionally associated regulatory polypeptides. The transcription factors themselves, or monoclonal antibodies raised against them, may be used for the identification of cell types that contain such regulatory polypeptides. Well known techniques may be employed to raise monoclonal antibodies.

Polynucleotides of the present invention corresponding to regulatory portions of the CD95 gene, or portions of such polynucleotides, may be used as probes to identify and isolate corresponding genomic regions from other species. Identification of such regions aids in identifying structurally conserved motifs which may also exhibit conserved function. Identification of conserved regulatory elements is an important predictive element for extrapolating experimental data from non-human sources to expression of the human CD95 gene.

Regulatory polynucleotides of the present invention are also useful for screening purposes to identify polynucleotides from non-human sources that exhibit homology to the identified sequences. The identification and isolation of CD95 regulatory polynucleotides makes possible the development of transgenic mammalian species having a modified CD95 gene structure lacking a silencer or enhancer regulatory region. Techniques such as homologous recombination and knockout strategies are well known. Such mammalian species are useful as models for studying CD95 gene regulation and apoptosis in vivo. Transgenic species with portions of a CD95 promoter or heterologous promoter having regulatory sequences of the present invention fused to a reporter gene may be used, for example, to analyze cross-species regulatory activities of the identified polynucleotide motifs in vivo. Transgenic species may also serve as in vivo models to screen for tissue specific modulators of CD95 expression. Transgenic species expressing a reporter gene, e.g. beta-galactosidase, which is driven by the CD95 promoter and enhancer, with or without silencer sequences, may also serve as in vivo models to screen for tissue specific modulators of CD95 expression. Compounds delivered to such transgenic species can be assayed for their in vivo effects on transcription of the reporter gene in the different constructs. In one mouse model of systemic autoimmunity, lpr homozygous mice, for example, the key abnormality is defective expression of the CD95 gene. (Abul K. Abbas, "Die and Let Live: Eliminating Dangerous Lymphocytes," *Cell* 84:655–657, 1996.)

Polynucleotides corresponding to regulatory portions of the CD95 gene and CD95 transcription factors also have numerous therapeutic applications. The CD95 enhancer and silencer polynucleotides may be used, for example, to co-express target/effector genes with native CD95 and thus target cells which can undergo apoptosis. CD95 regulatory polynucleotides cloned in front of the native CD95 gene promoter or a heterologous promoter could be used for regulated co-expression of inhibitors or stimulators of apoptosis in cell types which express CD95, some of which are also susceptible to activation induced cell death. Exemplary inhibitors of CD95 apoptosis are CrmA, a viral inhibitor of the ICE-like cysteine proteases involved in apoptosis, and a dominant negative mutant of the CD95-associated protein FADD. Expression of wildtype FADD can be used to induce apoptosis.

Polynucleotides of the present invention may also be used in gene therapy applications to enhance or silence CD95 expression. A minigene comprising CD95 minimal regulatory sequences which may include, for example, nucleotide positions −1032 to −1 in the hCD95 promoter (which are required for native expression) fused to CD95 cDNA, is useful for enhancing CD95 transcription and expression through gene therapy. Such a minigene may be introduced, for example, in reconstitution and gain-of-function gene therapy in CD95-deficient autoimmune patients. To reconstitute regulated expression of wildtype CD95 in the appropriate cell types of autoimmune patients with a CD95 mutation or expression defect, crude bone marrow cells (or a cell fraction enriched for lymphocytes) from a patient or a compatible donor could be transfected with a CD95 minigene, cloned in viral or non-viral vectors, and these cells reinjected into the patient after destruction of the patient's remaining, untransfected bone marrow cells by radio and-or chemotherapy. Other suitable gene and/or cell therapy approaches are known in the art.

Polynucleotides containing all or a portion of the enhancer or silencer regulatory sequences disclosed herein may also have therapeutic applications as competitors with endogenous binding proteins or transcription factors for regulatory binding sites on the CD95 gene. Suitable delivery techniques are known in the art. CD95 expression may be modulated in vitro or in vivo using this technique.

Similarly, transcription factors may be employed using competitive or anti-sense strategies to modulate CD95 expression. Degradation-stabilized phosphorthiodate oligonucleotides, containing silencer and/or enhancer sequences, could be encapsulated into liposomes and delivered to patients by injection intravenously or directly into a target site. Alternatively, retroviral or adenoviral vectors, or naked DNA expressing anti-sense RNA for enhancer and/or silencer transcription factors, could be delivered into patient's cells in vitro or directly into patients in vivo by appropriate routes. Suitable techniques are known in the art.

The word "polynucleotide(s)," as used herein, means a polymeric collection of nucleotides and includes DNA and RNA molecules, both sense and anti-sense strands, and comprehends cDNA, genomic DNA, and wholly or partially synthesized polynucleotides. Identification of human genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNAs corresponding to the identified sequences and variants may be produced by conventional synthesis methods. All of the polynucleotides described herein are isolated and purified.

The word "variant(s)," as used herein in connection with polynucleotides, comprehends polynucleotides having nucleotide sequences different from the specifically identified sequences, wherein one or more of the nucleotides is deleted or substituted, or one or more nucleotides are added, without appreciable loss of the regulatory activity of the identified sequence(s). Polynucleotide variants may be naturally occurring allelic variants, or non-naturally occurring variants. Variant polynucleotides preferably exhibit at least 50%, more preferably at least 70% and most preferably at least 90% identity to the identified regulatory sequences and cDNA sequences. Variant polynucleotides more preferably exhibit at least 70% and most preferably at least 90% identity to any 8 nucleotide contiguous portion of an identified regulatory sequence and any 50 nucleotide contiguous portion of an identified cDNA sequence. More preferably yet, variant polynucleotides differ from an identified regulatory or cDNA sequence by substitution, deletion or addition of five nucleotides or fewer. The identity of polynucleotides may be determined by comparing sequences using, for example, algorithms from the FASTA or BLAST search programs (GCG software package, University of Wisconsin) for cDNA comparisons and programs such as TFSEARCH (Yutaka Akiyama, Kyoto University), to search the Transfac database (GBF, Braunschweig, Germany) or search algorithms used in the TESS database, to compare regulatory sequences.

Regulatory polynucleotides and transcription factors are described herein with reference to activities involving "enhancing" or "silencing" transcription of coding portions of the CD95 gene or another gene appropriately linked to a regulatory polynucleotide sequence and a suitable promoter. Such regulatory activities are observed and may be assessed both in vitro and in vivo. It will be recognized that organisms and cells of different types, as well as cells in different developmental stages and physiological or in vitro conditions, may exhibit substantially different transcriptional activities. Regulatory polynucleotides described herein as having "enhancing" or "silencing" activities are described with reference to transcription of a CD95 gene having a CD95 basal promoter (−421/−1-CAT) or an HSV tk promoter. Transcriptional activity is considered to be "enhanced" or "silenced" when there is at least a 50%, and more preferably at least a 100%, change in the level of transcriptional activity in the presence of a regulatory polynucleotide compared to the transcriptional activity measured under substantially the same conditions in the presence of the CD95 basal promoter or the HSV tk promoter. Similarly, transcriptional activity is considered to be "enhanced" or "silenced" when there is at least a 50%, and more preferably at least a 100%, change in the level of transcriptional activity in the presence of a transcription factor or polynucleotide/transcription factor complex compared to the transcriptional activity measured under substantially the same conditions in the absence of a transcription factor or polynucleotide/transcription factor.

Proteinaceous transcription factors are described herein with reference to approximate molecular weights. "Approximate" molecular weights contemplate variances of up to 5% of stated molecular weights up to 50 kDa; variances of up to 10% of stated molecular weights from 51 kDa–100 kDa; and variances of up to 25% of stated molecular weights from 101–300 kDa. Binding of proteinaceous transcription factors to polynucleotides and formation of DNA/protein complexes may be assessed in vitro using standard EMSA techniques described below, or in vivo by measuring enhancement or silencing of transcription from the CD95 gene or another gene appropriately linked to a regulatory polynucleotide and a suitable promoter.

The words "isolated" and "purified," and other terms used herein, are used in accordance with their art-recognized meanings.

BRIEF DESCRIPTION OF THE DRAWINGS

Preferred embodiments of the applicants' invention will be described with reference to the drawings, in which:

FIGS. 1A–1C show results of the functional analysis of the hCD95 gene 5'-flanking region by transient transfection of CAT reporter constructs. Individual reporter constructs are illustrated, with construct names referring to nucleotide positions of the subcloned regions of the hCD95 gene. The results of transient transfections into HeLa and COS-7 cells are illustrated in lanes B and C, respectively. These results identify regions in the hCD95 gene that enhance (E1; −1007 to −964) and silence (S1; −1035 to −1008) transcription from the hCD95 promoter.

FIG. 1B illustrates the 5'-flanking region of the hCD95 gene, with restriction sites relevant for subcloning identified using the following abbreviations: H, Hind III; P, Pst I; and S, Sac II.

FIG. 7A shows UV-crosslinking using nuclear extracts from murine L929 cells with a double-stranded hCD95 enhancer region probe (SEQ ID NO: 1). Distinct DNA/protein complexes of approximately 59 and 113 kDA, and a high molecular weight complex of approximately 200–300 kDa are identified. FIG. 7B shows the results of UV-crosslinking using nuclear extracts from Jurkat and L929 cells with a single-stranded hCD95 silencer region probe (SEQ ID NO:2) to identify DNA/protein complexes of approximately 47, 77 and 100 kDa.

FIGS. 8A–8B illustrate the results of Southwestern analysis. FIG. 8A shows the results of Southwestern analysis using nuclear extracts from Jurkat and rat dermal papilla (rDP) cells with a double-stranded hCD95 enhancer region probe (SEQ ID NO:1). Distinct DNA/protein complexes of approximately 113 kDa (in Jurkat and rDP) and approximately 59 kDa (in rDP) were identified. FIG. 8B shows the results of Southwestern analysis using nuclear extracts from Jurkat cells with a single stranded silencer region probe (SEQ ID NO:2). Distinct DNA/protein complexes of approximately 47 kDa and 100 kDa were identified.

DETAILED DESCRIPTION OF THE INVENTION

Figure 1A:
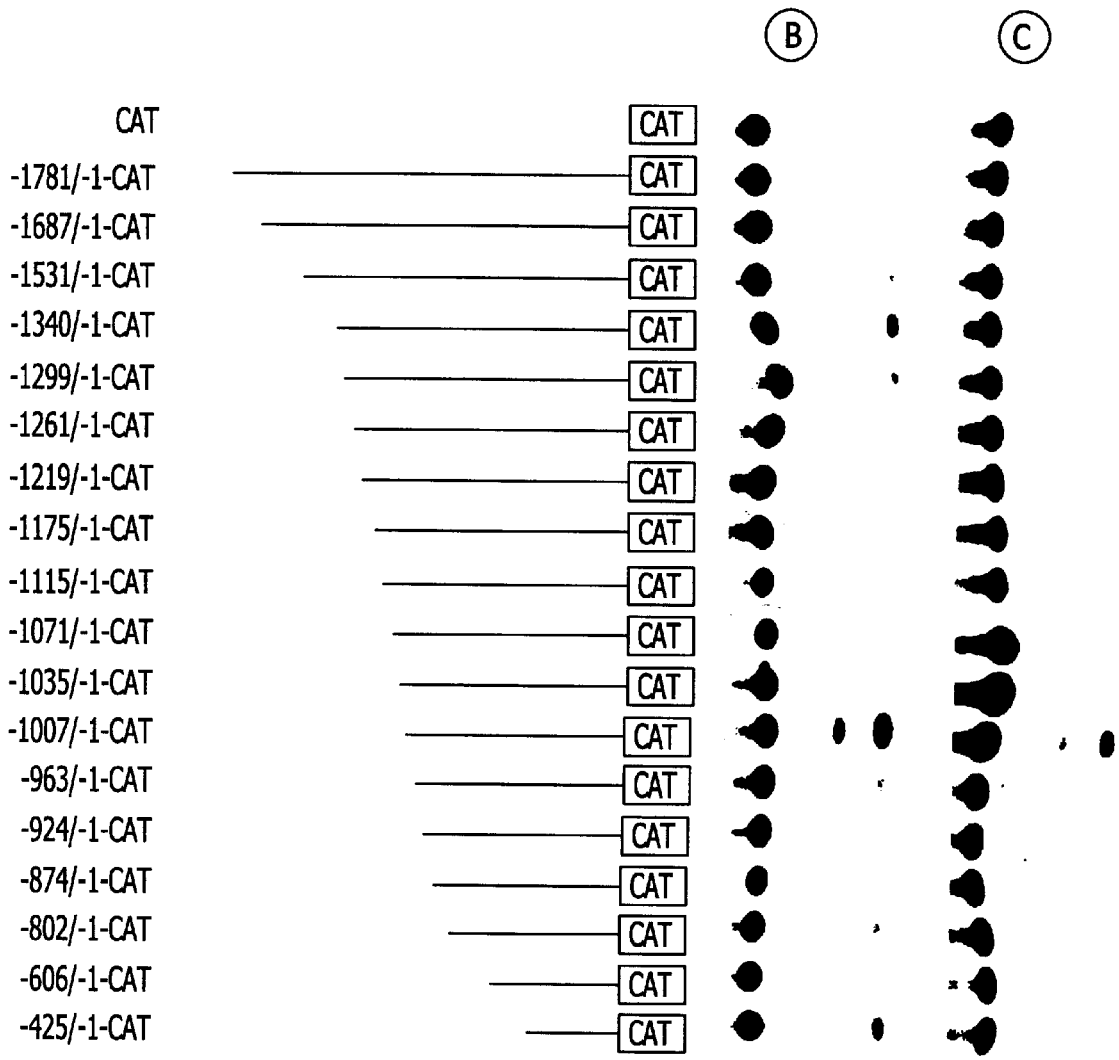

Genomic clones for the human CD95 (hCD95) gene were isolated and a 2.3 kb region of the hCD95 gene 5'-flanking region was sequenced. The hCD95 polynucleotide sequence is assigned accession number X87625 in the EMBL database. Initial functional analysis, using CAT reporter constructs and transient transfections, identified transcription silencer activity residing between nucleotide positions −1,781 and −1,007 of the hCD95 gene, and strong transcription enhancer activity residing between nucleotide positions −1,007 and −425 of the human CD95 gene. This experimental work is described in F. Rudert et al., "Identification of a Silencer, Enhancer, and Basal Promoter Region in the Human CD95 (Fas/APO-1) Gene," DNA AND CELL BIOLOGY, Vol. 14, No. 11, pp. 931–937, 1995. Additional functional analysis further delineated the enhancer and silencer regions. A transcription enhancer region, denominated E1 (SEQ ID NO:1), resides between nucleotide positions −1007 and −964 in the hCD95 gene, and a transcription silencer region, denominated S1 (SEQ ID NO:2), resides between nucleotide positions −1035 and −1008 in the hCD95 gene. These regions mediate cell type-specific and activation state-dependent transcriptional regulation of the CD95 gene during activation-induced cell death.

Further experimental work identified a hexameric inverted repeat binding sequence (IR2) (SEQ ID NO:5), present in the enhancer region (E1), that mediates sequence specific binding of nuclear factors present in several mammalian cell lines. Contributions of the individual nucleotide positions to binding were assessed and a degenerate enhancer consensus motif binding sequence (SEQ ID NO:3) was identified. Spacing derivatives of the enhancer region (E1) consensus motif binding sequence (identified in SEQ ID NOS:4, 6) also formed novel complexes with mammalian nuclear extracts. This data suggests the existence of a family of related transcriptional factors that recognize the same enhancer motif binding sequence, but have different spacing requirements. Enhancer region (E1) binding sequences autonomously enhanced transcription from the heterologous HSV thymidine kinase ("tk") promoter only in the absence and not in the presence of the silencer region, demonstrating the in vivo functionality of the regulatory sequence motifs. A heptamer motif binding sequence (SEQ ID NO:7), which is present in identical copies in the hCD95 enhancer and silencer regions, that may mediate binding of nuclear factor(s) to the silencer S1 region, was also identified.

Proteinaceous transcription factors that bind to CD95 regulatory polynucleotides have also been identified. UV cross-linking analysis using an hCD95 silencer probe (SEQ ID NO:2) showed cross-linked DNA/protein complexes of approximately 47, and 77 and 100 kDa with both mammalian and murine nuclear extracts. Results from probing a Western blot of Jurkat cell nuclear extract with a single stranded silencer probe suggested that the 47 and 100 kDa complexes corresponded to single nuclear proteins. Heptamer-containing silencer sequence competitor (SEQ IDS NO:12), complementary to the single stranded silencer probe (SEQ ID NO:2), but not competitor corresponding to the probe DNA strand (SEQ ID NO:13) competed for binding of the 47 and 100 kDa species. This correlates with results from EMSA experiments suggesting that the silencer DNA/protein complex is preferably or exclusively formed with single-stranded DNA and that double-strandedness of the DNA at or near the binding region prevents silencer complex formation. The complementary competitor (SEQ ID NO:12) either contains a silencer binding site (SEQ ID NO:7) and competes directly with the single-stranded silencer probe (SEQ ID NO:2) or prevents silencer factor binding by double-strand formation. UV cross-linking analysis using an enhancer probe (SEQ ID NO:1) and murine cell extract identified cross-linked DNA/protein complexes having molecular weights of about 113 kDa and 59 kDa, and a high molecular weight cross-linked DNA/protein complex of about 200–300 kDa. Southwestern analyses using the same silencer and enhancer probes produced similar results.

The present invention is illustrated by reference to the following experimental protocols and results identifying regulatory polynucleotides and transcription factors. The experimental protocols and results support the specification and claims and should not be construed to limit the invention, as claimed, in any fashion.

Identification of hCD95 Regulatory Polynucleotides
Isolating and Sequencing Genomic Clones for Human CD95

Clones (5×10⁵) of a human genomic phage library from placenta were screened with a cDNA probe corresponding to the coding region of hCD95 (EMBL database, accession number x87625). λ phages were grown on *E. coli* Tap90 and replica-plated onto Hybond N⁺ nylon filters (Amersham). After denaturation and fixing of the DNA, filters were hybridized with the random-primed probes in 40% formamide, 1M NaCl, 1% NaDodSO₄, 10× Denhardts, 50 mM TrisHCI pH 7.5,2 mM EDTA, 200 μg denatured salmon sperm DNA at 42° C. overnight. Filters were washed in 2× SSPE/0.1% NaDodSO₄ at 65° C. Positive phage clones were isolated after autoradiography and plaque-purified twice using the CD95 probe. A 3.7-kb Hind III fragment from a partial Hind III digest of purified phage DNA was identified by Southern analysis using oligonucleotide FR257 (SEQ ID NO:8) corresponding to positions −205 to −184 in hCD95 cDNA (Itoh et al., "The Polypeptide Encoded by the cDNA for Human Cell Surface Antigen Fas Can Mediate Apoptosis," *Cell* 66:233–243, 1991) and was subcloned in pBS SKII⁺ (Stratagene) and partially sequenced. The sequence was determined by PCR cycle sequencing using either ³²P-labeled primers or fluorescent-labeled dideoxy-nucleotides and a model 373A automated sequencer (Applied Biosystems).

Cloning of Initial Human CD95 Gene Reporter Constructs

A panel of 5' deletions of the 5'-flanking region of the human CD95 gene between positions −1781 and −425 was generated by PCR amplification from the genomic hCD95 clone described above. Several reporter constructs were made by cloning selected segments of the hCD95 gene in front of the chloramphenicol acetyl transferase (CAT) gene in the reporter plasmid pBLCAT8⁺ (Klein-Hitpass et al., "A 13 bp Palindrome is a Functional Estrogen Responsive Element and Interacts Specifically with Estrogen Receptor," *Nucleic Acids Res.* 16, 647–663, 1988). −1781/−67-tk-CAT was constructed by first ligating the 1.7-kb Hind III-Sac II fragment into the Hind III site of Hind III/Bam HI-digested pBLCAT8⁺ and then filling in and ligating the Sac II and Bam HI sites. −1007/−1-tk-CAT and −1007/−1-CAT were generated by inserting a Hind III/Bg/II-digested PCR fragment (Primers FR 283: SEQ ID NO:9 and FR 290: SEQ ID NO:10) into Hind III/Bam HI- and Hind III/Bg/II-digested pBLCAT8⁺, respectively. −1781/−1-CAT was constructed by cloning the 425-bp Pst I-Bg/II fragment from −1007/−1-CAT into Pst I/Bg/II digested −1781/−67-tk-CAT. −1781/−67-CAT was constructed by cutting −1781/−67-tk-CAT with Pst I/Bg/II, filling in the ends, and religating the vector. −425/−1-CAT was derived from −1007/−1-CAT by digestion with Hind III/Pst I, filling in the ends, and religation of the remaining vector. The PCR conditions were: 50 pmoles of each primer, 200 μM dNTPs each, 2 mM MgCl2, 10 mM TrisHCI pH 8.3, 50 mM KCI, and 2.5 units of Taq polymerase (Boehringer). Amplification was done for 1 min at 94° C., 1 min at 55° C., and 1.5 min at 72° C. for 30 cycles.

Cloning of Additional Human CD95 Gene Reporter Constructs

An additional panel of 5' deletions of the 5'-flanking region of the human CD95 gene between positions −1781 to −425 was generated by PCR amplification from the genomic hCD95 clone described above and cloned in front of the CAT gene in the reporter plasmid pBLCAT8⁺ which lacked the HSV thymidine kinase (tk) promoter. The following CAT reporter constructs were cloned: −1781/−1-CAT; −1687/−1-CAT; −1513/−1-CAT; −1340/−1-CAT; −1299/−1-CAT; −1261/−1-CAT; −1219/−1-CAT; −1175/−1-CAT; −1115/−1-CAT; −1071/−1-CAT; −1035/−1-CAT; −1007/−1-CAT; −963/−1-CAT; −924/−1-CAT; −874/−1-CAT; −802/−1-CAT; −606/−1-CAT; and −425/−1-CAT.

Deletion constructs were generated by PCR amplification using the fixed downstream primer identified in SEQ ID NO:9 with an attached BgI II-site and the following respective upstream primers:

| | |
|---|---|
| −1687/−1-CAT | SEQ ID NO.:20 |
| −1513/−1-CAT | SEQ ID NO.:21 |
| −1340/−1-CAT | SEQ ID NO.:22 |
| −1299/−1-CAT | SEQ ID NO.:23 |
| −1261/−1-CAT | SEQ ID NO.:24 |
| −1219/−1-CAT | SEQ ID NO.:25 |
| −1175/−1-CAT | SEQ ID NO.:26 |
| −1115/−1-CAT | SEQ ID NO.:27 |
| −1071/−1-CAT | SEQ ID NO.:28 |
| −1035/−1-CAT | SEQ ID NO.:29 |
| −963/−1-CAT | SEQ ID NO.:30 |
| −924/−1-CAT | SEQ ID NO.:31 |
| −874/−1-CAT | SEQ ID NO.:32 |
| −802/−1-CAT | SEQ ID NO.:33 |
| −606/−1-CAT | SEQ ID NO.:34 | containing a Hind III-site. Hind III/Bg/II-digested PCR fragments were gel-purified and cloned into the corresponding sites of pBLCAT8+. Construction of −1781/−1-CAT, −1007/−1-CAT and −425/−1-CAT reporter constructs is described above. The additional constructs were generated by ligating double-stranded oligonucleotides having SEQ ID NOS:4, 6, 11,19 or the same sequences with a 5' extension corresponding to SEQ ID NO:2, most of these oligonucleotides also containing a Hind III-compatible 5' overhang, into Hind III-digested pBLCAT8+. All constructs were confirmed by sequencing using an automated sequencer (Applied Biosystems).

Transient Transfection of CAT Reporter Constructs

COS-7 (Cynomologous monkey kidney) and HeLa (human cervix carcinoma) cells were cultured in standard Dulbecco's modified Eagle's medium (DMEM) supplemented with 5% fetal calf serum, penicillin, streptomycin, glutamine, and B-mercaptoethanol (2-ME). 5×10⁵ cells were seeded in 10-cm plastic culture dishes (Falcon) 24 hr prior to transfection. Cells were transfected by the CaPO₄ method with 5 μg of initial and additional reporter plasmids described above, 1.5 μg of β-galatosidase (β-Gal) expression vector pCH110 (Pharmacia) as internal control, and 8 μg of pBS (Stratagene) as carrier DNA. At 18 hr after transfection, cells were washed once with DMEM, fresh growth medium was added, and the cells incubated for another 24 hr. Thereafter, cells were harvested in 10 mM TrisHCI pH 7.5, 1 mM EDTA, 150 mM NaCl; spun down; resuspended in 250 mM TrisHCI pH 7.5, 1 mM EDTA, 15% glycerol; and extracts prepared by repeated freeze-thaw cycles. Chloramphenicol acetyl transferase (CAT) assays, normalized for β-Gal expression, were done as described in Zelent et al., "Cloning and Murine α and β Retinoic Acid Receptors and Novel Receptor γ Predominantly Expressed in Skin," *Nature* 339:715–717, 1989 using 0.5 mM acetyl CoA (Boehringer) and 0.2 μCi [¹⁴C]chloramphenicol (sp. act. 54 mCi/mmole, Amersham). The reaction products were separated by thin-layer chromatography in CHCl₃/methanol (95:5).

Functional Analysis of CD95 Gene Sequences

The CAT reporter constructs described above were used to functionally analyze the hCD95 gene 5'-flanking region in transient transfection assays. The percentage CAT conversion and average fold stimulation, compared to pBLCAT8+ lacking the tk promoter (set as 1), are shown below for transfections of the initial reporter constructs into COS-7 and HeLa cells.

TABLE 1

| | COS-7 | | HeLa | |
|---|---|---|---|---|
| Construct | % CAT Conversion | Fold Stimulation | % CAT Conversion | Fold Stimulation |
| tk-CAT | 2.5 ± 1 | 6 | 4.9 ± 4.9 | 10 |
| -1781/-67-tk-CAT | 1.8 ± 0.7 | 5 | 5.2 ± 4.6 | 11 |
| -1007/-1-tk-CAT | 12.3 ± 5.2 | 31 | 50.7 ± 24.7 | 102 |
| CAT | 0.4 ± 0.1 | 1 | 0.5 ± 0.4 | 1 |
| -1781/-1-CAT | 0.6 ± 0.2 | 2 | 2.1 ± 0.6 | 4 |
| -1781/-67-CAT | 0.8 ± 0.4 | 2 | 4.4 ± 1.9 | 9 |
| -1007/-1-CAT | 7.6 ± 4.1 | 19 | 29.7 ± 19.0 | 60 |
| -425/-1-CAT | 3.2 ± 0.4 | 8 | 6.6 ± 0.6 | 13 |

The largest construct tested (-1781/-1-CAT) showed only very weak activity in COS-7 and HeLa cells. The same construct, with a 67-bp deletion at its 3' end (1781/-67-CAT) gave practically the same response as -1781/-1-CAT in COS-7 cells and an approximately two-fold increase in HeLa cells. When tested together with the heterologous HSV tk promoter, the same fragment (-1781/-67-tk-CAT) showed no additional transcriptional activity compared to that observed with the tk promoter alone in both COS-7 and HeLa cells. However, a truncation of 764 bp (-1007/-1-CAT) at the 5' end of -1781/-1-CAT increased transcriptional activity 19-fold and 60-fold above background levels in COS-7 and HeLa cells, respectively. A similar upregulation was seen with a tk promoter-containing, identical construct (-1007/-1-tk-CAT) in both cell lines. These data indicated that a silencer is located between positions -1,781 and -1,007 in the human CD95 gene 5'-flanking region. A further truncation of 582 bp at the 5' end of reporter -1007/-1-CAT drastically attenuated the strong activity seen with the construct, but -425/-1-CAT retained a basal promoter activity above that observed with -1781/-1-CAT and -1781/-67-CAT. These results demonstrate the presence of an enhancer between -1,007 and -425 in the hCD95 gene 5'-flanking region and revealed a basal promoter activity in the first 425 bp of the hCD95 regulatory region. Basal promoter activity reached a level comparable to that of the tk promoter. Thus, the hCD95 promoter was regarded as relatively strong.

Figure 1B:

Functional analysis of the hCD95 gene 5'-flanking region by transient transfection of the additional CAT reporter constructs is illustrated in FIG. 1. Individual reporter constructs are illustrated, with construct names referring to nucleotide positions of the subcloned regions of the hCD95 gene. The results of transient transfections into the HeLa and COS-7 cells are illustrated in lanes B and C, respectively. The thin layer chromatograms show the amount of acetylated $^{14}C$-chloramphenicol substrate as generated by the level of CAT enzyme expressed from the respective reporter constructs, where spot intensity correlates with the level of transcriptional activation. These data further delineate regions in the hCD95 gene which enhance (E1; -1007 to -964) or silence (S1; -1035 to -1008) transcription from the CD95 promoter. The results from transfection analysis indicate that the CD95 silencer represses transcription to levels of about 3-fold less than seen with the CD95 basal promoter (-425/-1-CAT), which has a transcriptional activity similar to that of the HSV tk promoter. The CD95 enhancer increases transcription from the CD95 basal promoter about 2- to 4-fold and from the HSV tk promoter about 5 to 10 fold, depending on the cell type.

Delineation of additional regulatory polynucleotides is described below in connection with the identification of transcription factors.

Determination of hCD95 Transcriptional Start Sites
Primer Extension Analysis Total RNA from Jurkat cells, rat lung cells and rat small intestine cells was extracted according to Chomczynski and Sacchi, "Single Step Method of RNA Isolation by Acid Guanidinium Thiocyanate-Phenol-Chloroform Extraction," *Anal. Bio-Chem*, 162:156–159, 1987. All subsequent steps were performed using diethylpyrocarbonate-treated $H_2O$. For primer annealing, 10 µg total RNA together with 5 pmole γ-$^{32}P$-labeled primer FR257 (SEQ ID NO: 8, $3 \times 10^5$ cpm) were incubated for 5 min. at 65° C. in hybridization buffer (150 mM KCl, 10 mM TrisHCl pH 8.3, 1 mM EDTA) in a total volume of 15 µl and the mixture then slowly cooled to room temperature for 1.5 h. To this, 30 µl of primer extension buffer [30 mM TrisHCl pH 8.3, 15 mM $MgCl_2$, 8 mM DTT, 0.22 mg/ml actinomycin D, 220 µM dNTPs, 200 units MMLV reverse transcriptase (BRL)] were added and reverse transcription was carried out at 42° C. for 1 h. Then, 105 µl of RNAse digestion buffer [20 µg/ml DNase-free RNaseA (BRL), 100 µg/ml sonicated salmon sperm DNA (Sigma), 100 mM NaCl, 10 mM TrisHCl pH 7.5, 1 mM EDTA] were added, followed by digestion at 37° C. for 15 min. 15 µl of 3M sodium acetate were added, the sample extracted with phenol/$CHCl_3$ and the DNA was precipitated with ethanol. The extension products were resuspended in formamide loading buffer, heat-denatured and separated on a 6% sequencing gel.

Identification of Transcriptional Start Sites

Figure 2:
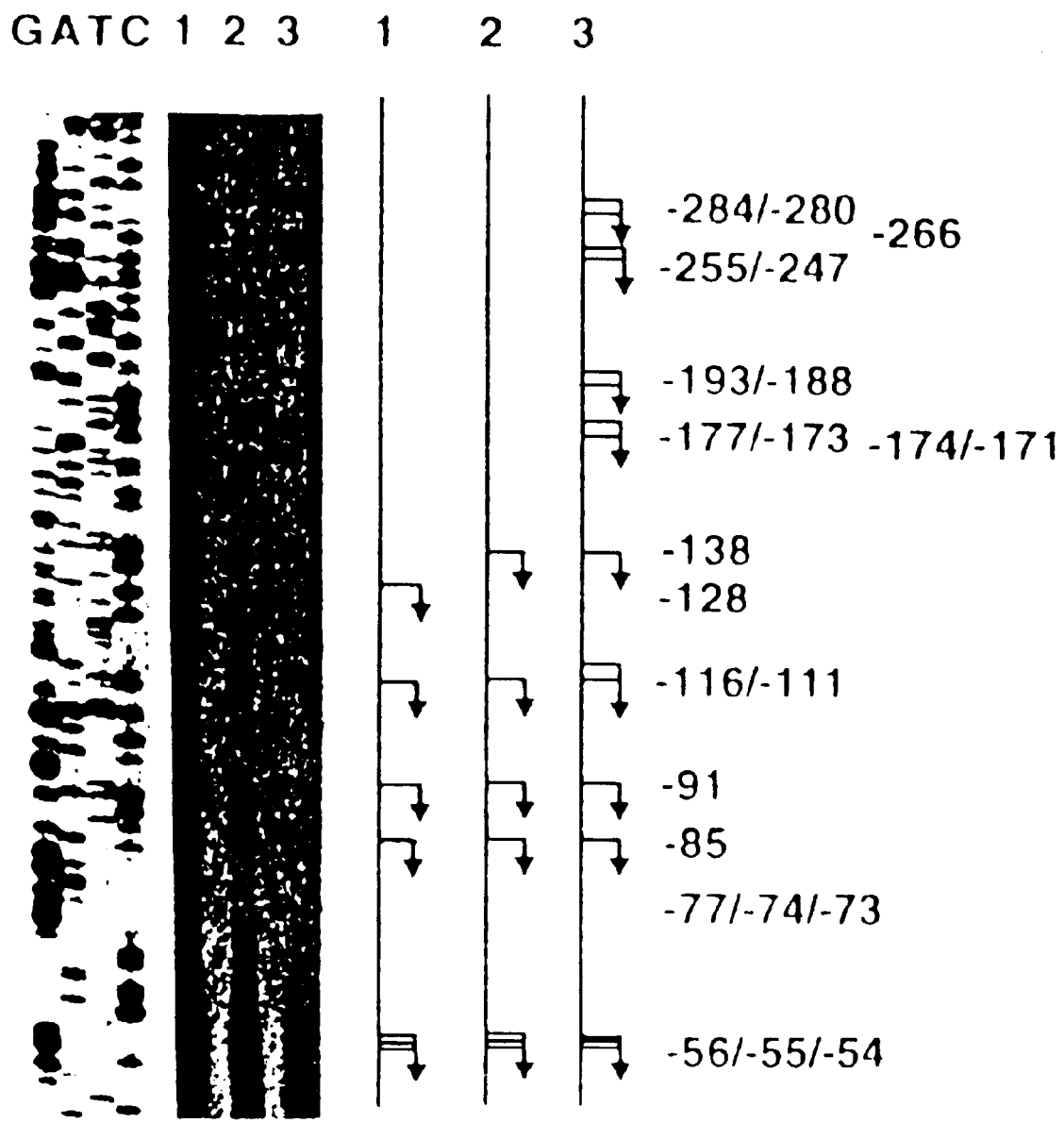
FIG. 2 illustrates the identification of transcriptional start sites for the hCD95 gene by primer extension analysis on total RNA from Jurkat cells (lane 1), rat lung cells (lane 2) and rat small intestine cells (lane 3). Numbers at the right refer to nucleotide positions upstream of the translational start site in the hCD95 gene.

In Jurkat cells, multiple putative transcriptional start sites were identified clustered from -54 to -128 (FIGS. 2A,B lane 1) on the hCD95 gene. These matched most of the transcriptional start sites that have been detected in human spleen (Behrmann et al., "Structure of the Human APO-1 Gene," *Eur. J. Immunol.* 24:3057–3062, 1994) using 5' RACE PCR. Virtually the same extension products were obtained with RNA extracted from rat lung (FIGS. 2A,B, lane 2), showing that primer FR257 (SEQ ID NO:8), which spans the ATG in hCD95, could hybridize to rat CD95 mRNA and suggesting that certain start sites are conserved in human and rat CD95 genes. When RNA from rat small intestine was used, additional extension products, not seen in Jurkat cells or rat lung, were obtained (FIGS. 2A,B lane 3). Some of these new, putative start sites lie in very close proximity to hCD95 gene start sites identified in the human T-cell lines CEM-6 and Molt-4 (Cheng et al., "Characterization of the Human Fas Gene," *J Immunol.* 154:1239–1245, 1995) also using primer extension analysis.

Identification of Transcription Factors Which Bind to Regulatory hCD95 Polynucleotides Electrophoretic Mobility Shift Assay (EMSA) Protocol Nuclear extracts were prepared from Jurkat (human T lymphoma cells) and MP-1 (human EBV-transformed B cells) grown under 5% $CO_2$ in RPMI 1640 medium supplemented with antibiotics and 5% fetal bovine serum, and from HeLa, COS-7, CV-1 (COS-7 derivative) and L929 (murine fibroblast cells) grown under 10% $CO_2$ in DMEM medium supplemented with antibiotics and 5% fetal bovine serum according to the method of Andrews and Faller, "A Rapid Micropreparation Technique for Extraction of DNA-Binding Proteins from Limiting Numbers of Mammalian Cells," Nucleic Acids Research, Vol. 19, No. 9, 1991. If not indicated otherwise, binding reactions contained 5 µg nuclear extract (adjusted to give an equal contribution of 40 mM NaCl in the binding reaction), 150 mM (or 100 mM) KCI, 2 µg of non-specific competitor DNA (poly[d(1-C)] or poly[d(A-T)], as indicated), 12% glycerol, 12 mM Hepes pH 7.9, 4 mM Tris-HCI pH 7.9, 1 mM EDTA, 1 mM dithiothreitol, 20 fmole of [γ-$^{32}$P]ATP-labeled probe (double- or single-stranded, as indicated). The indicated amounts of competitor oligonucleotides were added before addition of the nuclear extract and the reaction incubated for 30 min. at room temperature. Three µl loading buffer (12% glycerol, 12 mM Hepes pH 7.9, 4 mM Tris-HCI pH 7.9, 1 mM EDTA, 1 mM dithiothreitol, 0.1% bromophenol blue) were added, the reactions loaded on pre-run (2 h at 150 V) non-denaturing 4% polyacrylamide gels (acrylamide:bisacrylamide, 30:1). The gels were run in 50 mM Tris-HCI (pH 8.5), 380 mM glycine, 2 mM EDTA at 150 V (constant voltage) with water-cooling. Gels were dried and autoradiographed for 1 to 4 days. This assay, and variants of this assay are referred to herein as the "standard EMSA assay protocol."

Identification of Transcription Factors Which Bind to hCD95 Enhancer Region

Figure 3:
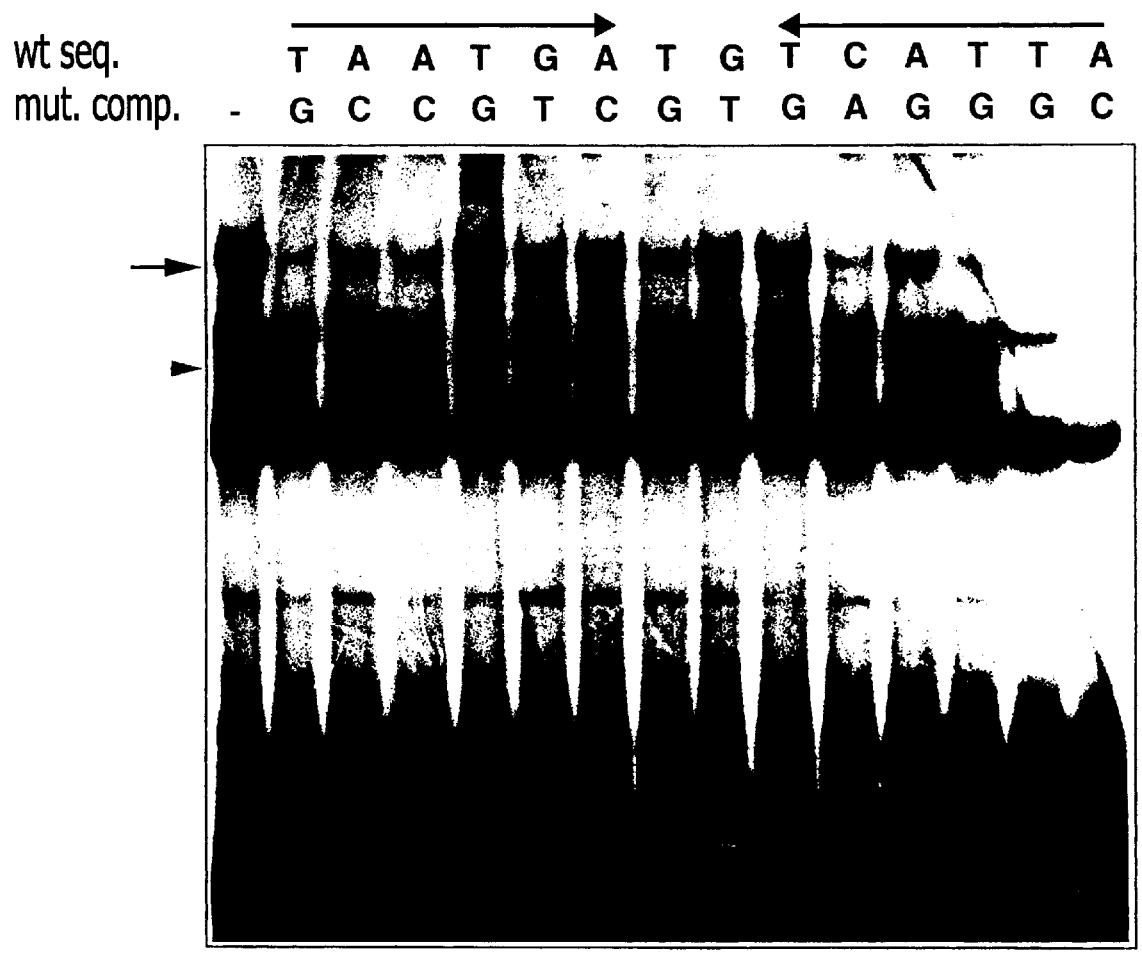
FIG. 3 illustrates the results of electrophoretic mobility shift assay (EMSA) analysis demonstrating that a hexameric inverted repeat sequence identified in SEQ ID NO:5 (IR2), present in the hCD95 enhancer region, mediates sequence specific binding of transcription factors in Jurkat cell nuclear extract. Distinct DNA/protein complexes are marked by an arrow and arrowhead. Mutational scanning of the hexameric inverted repeat identified in SEQ ID NO:5, as shown above the lanes, defined the contributions of individual nucleotide positions to binding and established the degenerate enhancer consensus motif polynucleotide sequence identified in SEQ ID NO: 3.

EMSA analysis using an E1 double-stranded probe (E1 probe, SEQ ID NO:11) and Jurkat cell nuclear extract revealed that a hexameric inverted repeat nucleotide, identified in SEQ ID NO:5 and present in E1, mediates sequence-specific binding of nuclear factors. Experimental results are shown in FIG. 3. Distinct DNA/protein complexes formed with these nuclear factors, referred to herein as transcription factors, are marked by an arrow and an arrowhead. Transcription factors that bind to the enhancer region hexameric inverted repeat (IR2) identified as SEQ ID NO:5 are also present in murine L929 cells and other primate and rodent cells, including HeLa, MP-1, COS-7, and rat dermal papilla (rDP) cells.

Mutational scanning of the enhancer region hexameric inverted repeat identified as SEQ ID NO:5, using a 50-fold molar excess of double stranded competitor oligonucleotides containing the single nucleotide substitutions indicated above the respective lanes (derivatives of SEQ ID NO:11) in EMSA analysis together with the wildtype enhancer probe (SEQ ID NO:1, See FIG. 3) has identified the importance of individual nucleotides for binding and defined the degenerate E1 consensus motif identified in SEQ ID NO:3 as an hCD95 enhancer region (E1) binding site.

Figure 4:
FIG. 4 illustrates the results of EMSA analysis demonstrating that novel DNA/protein complexes were formed in a sequence-specific manner. Complexes formed with hCD95 enhancer region motifs spaced by 1 bp and 4 bp are marked by an open arrowhead. This data suggests the existence of a family of related transcription factors which recognize the same binding motif but have different spacing requirements.

Identification of Transcription Factors which Bind to Spacing Derivatives of hCD95 Enhancer Region Using nuclear extracts from murine L929 cells in EMSA analysis, sequence-specific formation of novel DNA/protein complexes, which were different from enhancer region binding site IR2 complexes, was demonstrated with enhancer region sequence motifs spaced by 1 bp (IR1; SEQ ID NO:4) and 4 bp (IR4; SEQ ID NO:6). Experimental results are shown in FIG. 4. Complexes formed by the nuclear transcription factors that bind to hexameric inverted repeat (SEQ ID NO:5), containing enhancer probe (IR2, SEQ ID NO:11), are marked by an arrow and arrowhead. The open arrowhead indicates the presence of complexes formed by the enhancer region spacing derivatives (IR1; SEQ ID NO:4 and IR4; SEQ ID NO:6). The enhancer region IR1, IR2 and IR4 elements cross-competed for the formation of the respective DNA/protein complexes in a sequence-specific manner.

These results suggest the existence of a family of related transcription factors which recognize the same CD95 enhancer region binding motif but have different spacing requirements.

Identification of Transcription Factors which Bind to the S1 Region

Figure 5:
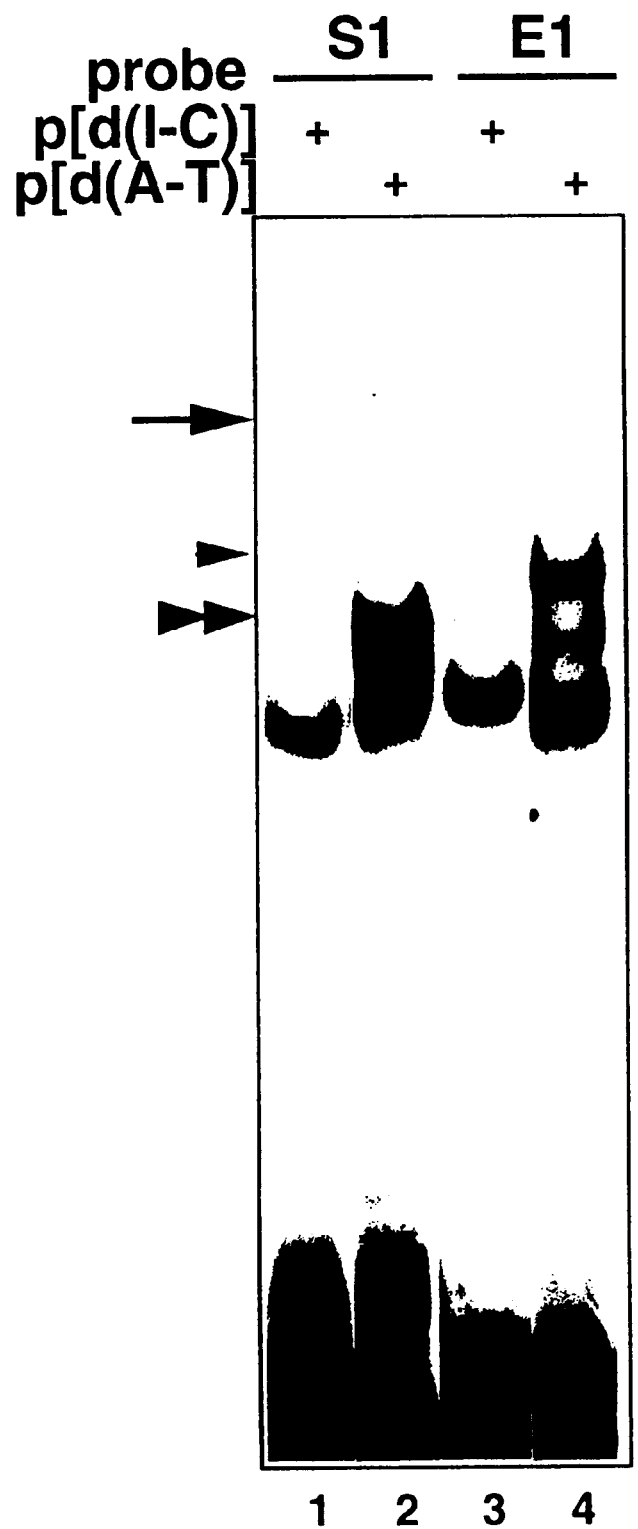
FIG. 5 illustrates the results of EMSA analysis demonstrating that a novel DNA/protein complex was formed with an hCD95 silencer region probe and an enhancer probe. The experimental work suggested that the polynucleotide heptamer motif identified as SEQ ID NO:7 mediates interaction with transcription factor(s).

Novel DNA/protein complexes were formed using a silencer region probe (SEQ ID NO:2), and an enhancer region IR2 probe (SEQ ID NO:11) when using polydAdT instead of polydIdC as non-specific competitor DNA in EMSA analysis. Results are shown in FIG. 5, with the silencer probe identification shown above the lanes and the double arrowhead indicating the novel complex. This factor (s) also bound to single-stranded silencer probes or was competed out by single-stranded silencer and enhancer probes.

Figure 6:
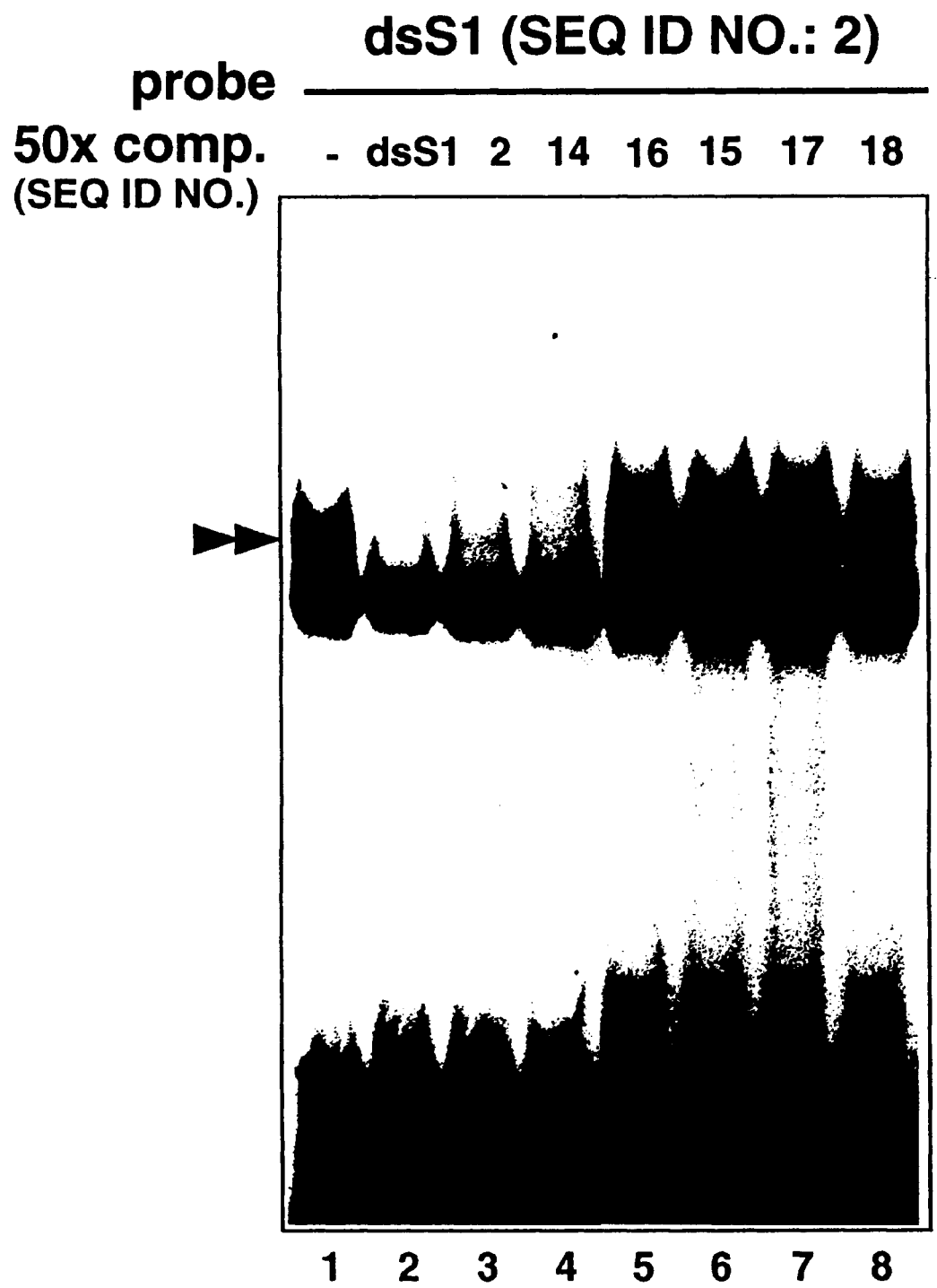
FIG. 6 illustrates the results of EMSA analysis demonstrating that single-stranded probes compete for complex-formation and interruption of the heptamer motif identified as SEQ ID NO:7 in the silencer region abolishes the ability of the probe to compete with wild-type silencer probe for complex formation. The polynucleotide heptamer motif is thus important for regulators silencing function. The SEQ ID NOS: for the probe sequences are identified above the lanes.

Further EMSA analysis is illustrated in FIG. 6, using silencer probes having SEQ ID NOS:2 and 14–18. The silencer region heptamer motif (SEQ ID NO:7), which is present in identical copies in the S1 and E1 regions, appeared to mediate interaction with the transcription factor (s), since the respective DNA/protein complex was also formed with a single-stranded silencer region probe (SEQ ID NO:12) including the silencer region heptamer sequence, but not with the complement of this probe (SEQ ID NO:13). Silencer region probes from both DNA strands, having an interruption of the heptamer motif in the silencer region and containing less than a full heptamer motif, identified in SEQ ID NOS:15–18, showed greatly reduced ability to compete for complex formation with the wildtype S1 probe.

Characterization of Transcription Factors for Silencer/Enhancer Regions by UV-crosslinking UV-crosslinking was performed essentially as described by Miyamoto et al., *Methods Enzymol.* 254, 633–641, 1995. Oligonucleotides of 44 and 28 bases in length were end-labeled as in the above-described EMSA reactions. Double-stranded DNA probes were prepared by annealing the end-labeled oligonucleotides and filling in with [γ-$^{32}$P]dATP, [γ-$^{32}$P]dCTP, [γ-$^{32}$P]dGTP (800 Ci/mmol) and 5-bromo-2'-dUTP using Klenow (Miyamoto et al., 1995.)

A standard EMSA binding reaction was set up with 40 fmol probe and 10 µg nuclear extracts ±4 pmol competitor DNA in a total volume of 40 ml in a flat-bottomed microtitre plate. The plate was covered with Saran-wrap and placed on ice. The reactions were irradiated for 60 minutes by inverting a UV transilluminator of 305 nm wavelength, such that the illuminator was within 5 cm from the microtitre plate.

The reactions were then divided into two. One aliquot was run on a 4% non-denaturing gel as described previously, and the second aliquot was run on a 10% reducing SDS-PAGE gel with $^{14}$C-labeled protein markers. The gels were dried followed by autoradiography with an intensifying screen for 1–3 days.

Figure 7A:
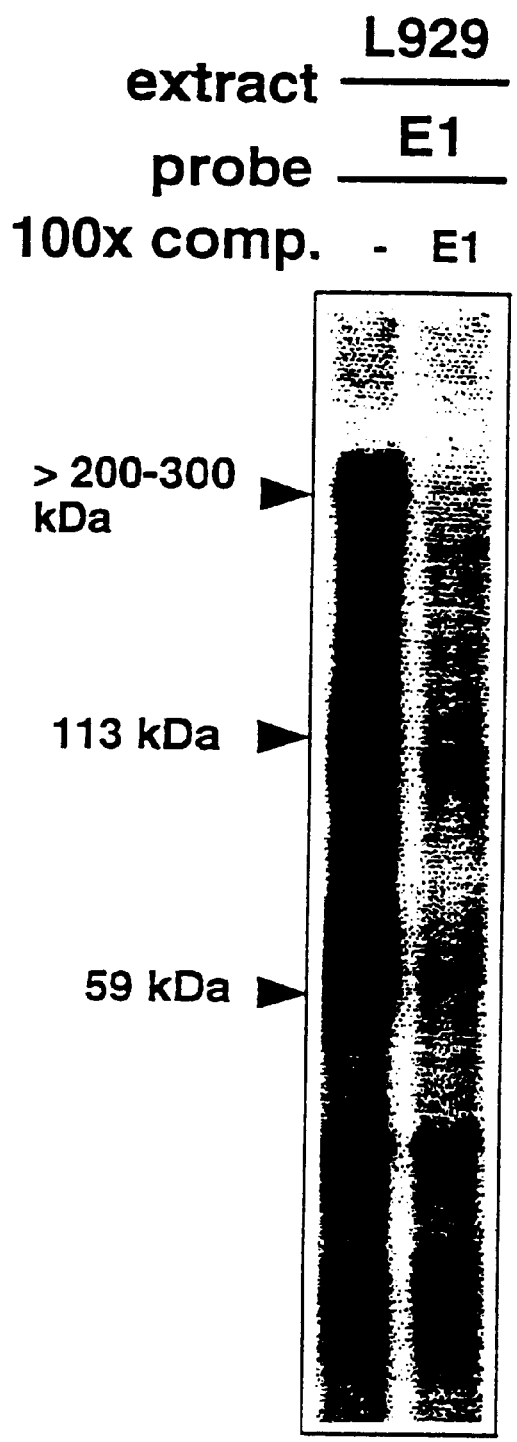
FIGS. 7A–7B illustrate the results of UV-crosslinking analysis.
Figure 7B:
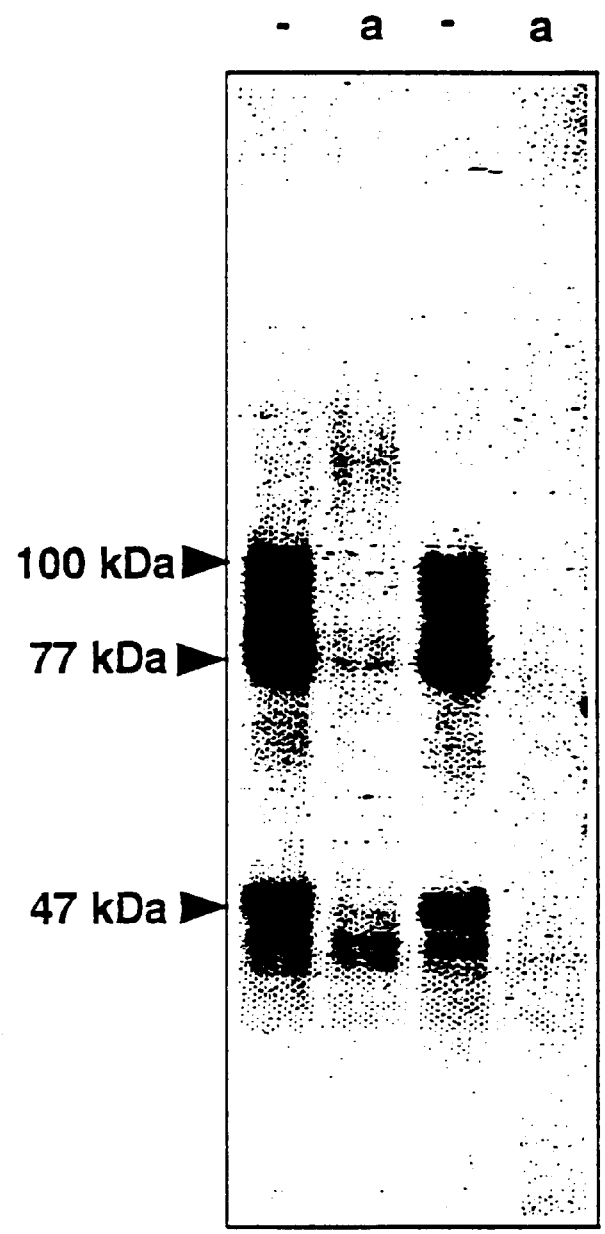

UV-crosslinking analysis results shown in FIG. 7B using an end-labeled, single-stranded S1 probe (SEQ ID NO:2), revealed cross-linked DNA/protein complexes of approximately 47, 77 and 100 kDa in Jurkat and L929 cells. Results from probing a Western blot of Jurkat cell nuclear extract with the single-stranded S1 probe (SEQ ID NO:2) suggested that the 47 kDa complex corresponded to a single nuclear protein. UV-crosslinking with a double-stranded E1 probe (SEQ ID NO:1), shown in FIG. 7A, revealed cross-linked DNA/protein complexes of approximately 59 kDa, 113 kDa, and a high molecular weight complex of approximately 200 to 300 kDa in L929 cells.

Characterization of Transcription Factors for Silencer/Enhancer Regions by Southwestern Analysis 20–40 μgs of nuclear extracts from Jurkat, L929 and rat dermal papilla (rDP) cells, prepared as described above, were electrophoresed on a 8–10% reducing SDS-PAGE gel with $^{14}$C-labeled protein markers. The gel was pre-soaked in Transfer Buffer prior to electroblotting to 0.2 mm nitrocellulose filters as described by Li, M. and Desiderio, S., Appendix 1, "Transcription Factors: A Practical Approach" (D. S. Latchman, Ed.) *IRL Press, Oxford*, pp. 187–196, 1993. Nitrocellulose filters were blocked in 2.5% (w/v) dried milk powder, 25 mM Hepes (pH 8), 1 mM DTT, 10% (v/v) glycerol, 50 mM NaCl, 1 mM EDTA at 4° C. for 18 hours. Filters were hybridised in SW-Binding Buffer (12% (v/v) glycerol, 12 mM Hepes (pH 8), 4 mM Tris-HCl (pH 8), 1 mM EDTA, 1 mM DTT, 40 mM NaCl, 100 mM KCl), 1 pmol/ml $^{32}$P-labeled DNA probe (end labeled or filled in, as above), 10 μg/ml non-specific competitor DNA (i.e. poly [dl-dC] or poly[dA-dT]) and ±100 pmol/ml competitor DNA for 60 minutes at room temperature. The filters were washed for 4×7 minutes in SW-Binding Buffer at 4° C., prior to autoradiography for 3 days with an intensifying screen.

Southwestern analysis results of Jurkat and rDP nuclear extracts using a double stranded enhancer probe (SEQ ID NO:1) are illustrated in FIG. 8A. These results show protein species having molecular weights of approximately 59 kDa (rDP) and 113 kDa (Jurkat and rDP) to which a double-stranded enhancer probe binds. Southwestern analysis results of Jurkat nuclear extracts using a single stranded silencer probe (SEQ ID NO:2) are illustrated in FIG. 8B. These results show protein species having molecular weights of approximately 47 kDa and 100 kDa to which a single-stranded silencer probe binds. Binding of the silencer probe to these proteins is greatly reduced or absent in the presence of a heptamer-(SEQ ID NO:7) containing competitor (SEQ ID NO:12), complementary to the probe strand, but not an equivalent competitor (SEQ ID NO:13) corresponding to the probe strand. These Southwestern results are consistent with UV-crosslinking and EMSA results obtained with the probes and competitors described above.

Figure 9:
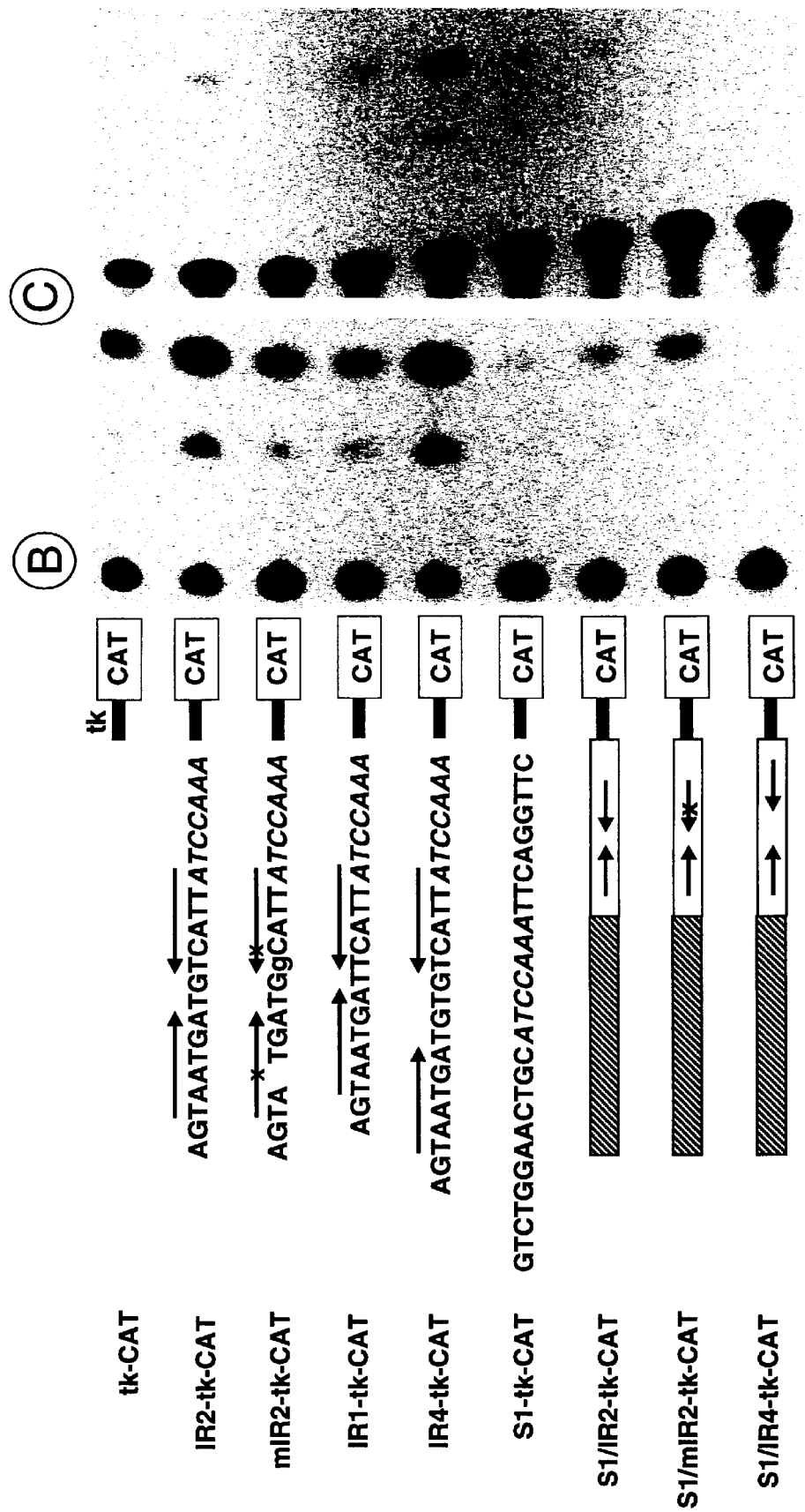
FIG. 9 show results of the transient transfection of CAT reporter constructs including various hCD95 enhancer and silencer region polynucleotides. Individual reporter constructs including those referred to as IR2-tk-CAT (SEQ ID NO:36), mIR2-tk-CAT (SEQ ID NO:19), IR1-tk-CAT (SEQ ID NO:37), IR4-tk-CAT (SEQ ID NO:38) and S1-tk-CAT (SEQ ID NO:2), are illustrated, with construct names referring to the hCD95 enhancer and/or silencer region polynucleotides. The results of transient transfections into HeLa and COS-7 cells are illustrated in lanes B and C, respectively. The hCD$^{95}$ enhancer polynucleotides autonomously enhance transcription from the heterologous tk promoter only in the absence of the silencer region. These results demonstrate the in vivo functionality of the identified hCD95 enhancer and silencer regions.

Demonstration of Promoter Context-Independent Function if hCD95 Silencer and Enhancer Regions CD95 enhancer binding site sequences IR1 (SEQ ID NO:4), IR2 (SEQ ID NO:11), mutated IR2 (SEQ ID NO:19), and IR4 (SEQ ID NO:6) were cloned, with and without an upstream silencer region (SEQ ID NO:2), in front of the HSV tk promoter and CAT gene in reporter plasmid pBLCAT8+. The S1/mIR2-tk-CAT construct had an additional base in the mIR2 region and is set forth in SEQ ID NO:35. The reporter constructs and results of transient transfection assays of these CAT reporter constructs into HeLa (B) and COS-7 (C) cells are shown in FIG. 9. The experimental results show that enhancer region elements in IR1, IR2 and IR4 autonomously enhanced transcription, to various extents, from the heterologous promoter only in the absence, and not in the presence, of silencer region polynucleotides. This demonstrates the in vivo functionality of the identified silencer and enhancer polynucleotide sequences.

All references and other materials cited herein are incorporated by reference in their entirety. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

---

We claim:

1. An isolated polynucleotide selected from the group consisting of the polynucleotides set forth as SEQ ID NOS:1–6, 11, 12 and 14.

2. An isolated polynucleotide according to claim 1 that, when operably linked to a CD95 gene, enhances transcription from the CD95 gene.

3. An isolated polynucleotide according to claim 1 that, when operably linked to a CD95 gene, silences transcription from the CD95 gene.

4. An isolated polynucleotide of claim 1 which is a DNA molecule.

5. An isolated polynucleotide consisting of the polynucleotide sequence set forth as SEQ ID NO:7.

6. An isolated polynucleotide selected from the group consisting of the polynucleotides set forth as SEQ ID NOS:1–7, 11, 12 and 14, that forms a DNA/protein complex with a proteinaceous transcription factor, whereby the presence of the DNA/protein complex in a DNA construct comprising a coding portion of the CD95 gene modulates expression of the CD95 gene.

7. An isolated polynucleotide according to claim 6 that forms a DNA/protein complex having a molecular weight of approximately 47, 77 or 100 kDa with a proteinaceous transcription factor, whereby the presence of the DNA/protein complex in a DNA construct comprising a coding portion of the CD95 gene silences expression of the CD95 gene.

8. An isolated polynucleotide according to claim 6 that forms a DNA/protein complex having a molecular weight of approximately 59, 113 or 200–300 kDa with a proteinaceous transcription factor, whereby the presence of the DNA/protein complex in a DNA construct comprising a coding portion of the CD95 gene enhances expression of the CD95 gene.

9. A DNA construct comprising, in the 5'-3' direction, an isolated polynucleotide selected from the group consisting of the polynucleotides set forth as SEQ ID NOS:1–7, 11, 12 and 14 operably linked to a gene promoter sequence and a coding portion of a gene.

10. A DNA construct of claim 9 wherein the gene is a CD95 gene.

* * * * *

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 44 base pairs
      (B) TYPE: nucleic acid
      (C) STRANDEDNESS: single
      (D) TOPOLOGY: linear (xi) SEQUENCE DESCRIPTION: SEQ ID NO:1:

AGTAATGATG TCATTATCCA AACATACCTT CTGTAAAATT CATG       44

(2) INFORMATION FOR SEQ ID NO:2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:2:

```
GTCTGGAACT GCATCCAAAT TCAGGTTC                                              28
```

(2) INFORMATION FOR SEQ ID NO:3:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:3:

```
KMMTGAKGTM AKM                                                              13
```

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:4:

```
AGTTAATGAT TCATTATCCA AA                                                    22
```

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:5:

```
TAATGATGTC ATTA                                                             14
```

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:6:

```
AGTTAATGAT GTGTCATTAT CCAAA                                                 25
```

(2) INFORMATION FOR SEQ ID NO:7:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (xi) SEQUENCE DESCRIPTION: SEQ ID NO:7:

```
TTTGGAT                                                                      7
```

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:8:

TGCCCAGCAT GGTTGTTGAG C                                  21

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:9:

CAAGATCTGG TTGTTGAGCA ATCCTC                            26

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:10:

GCGAAGCTTA GTAAATGATG TCATTATCC                          29

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:11:

AGTTAATGAT GTCATTATCC AAA                              23

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:12:

GAATTTGGAT GCAG                                          14

(2) INFORMATION FOR SEQ ID NO:13:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:13:

CTGCATCCAA ATTC                                          14

(2) INFORMATION FOR SEQ ID NO:14:

```
     (i) SEQUENCE CHARACTERISTICS:
         (A) LENGTH: 28 base pairs
         (B) TYPE: nucleic acid
         (C) STRANDEDNESS: single
         (D) TOPOLOGY: linear (xi) SEQUENCE DESCRIPTION: SEQ ID NO:14:

GAACCTGAAT TTGGATGCAG TTCCAGAC                                      28

(2) INFORMATION FOR SEQ ID NO:15:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (xi) SEQUENCE DESCRIPTION: SEQ ID NO:15:

GTCTGGAACT GCAT                                                     14

(2) INFORMATION FOR SEQ ID NO:16:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (xi) SEQUENCE DESCRIPTION: SEQ ID NO:16:

ATGCAGTTCC AGAC                                                     14

(2) INFORMATION FOR SEQ ID NO:17:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (xi) SEQUENCE DESCRIPTION: SEQ ID NO:17:

CCAAATTCAG GTTC                                                     14

(2) INFORMATION FOR SEQ ID NO:18:

(i) SEQUENCE CHARACTERISTICS:
         (A) LENGTH: 14 base pairs
         (B) TYPE: nucleic acid
         (C) STRANDEDNESS: single
         (D) TOPOLOGY: linear (xi) SEQUENCE DESCRIPTION: SEQ ID NO:18:

GAACCTGAAT TTGG                                                     14

(2) INFORMATION FOR SEQ ID NO:19:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO:19:

AGTATGATGG CATTATCCAA A                                             21

(2) INFORMATION FOR SEQ ID NO:20:

(i) SEQUENCE CHARACTERISTICS:
         (A) LENGTH: 20 base pairs
```

```
        (B) TYPE: nucleic acid
        (C) STRANDEDNESS: single
        (D) TOPOLOGY: linear (xi) SEQUENCE DESCRIPTION: SEQ ID NO:20:

CACATATGTG AGTTGCTGGC                                           20

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:21:

GCGAAGCTTC TTTTCATTTT GGAATAG                                   27

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:22:

GCGAAGCTTA GGTGGAACAG AGACAAGC                                  28

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:23:

GCGAAGCTTT GGTAAGTGCA GTGAC                                     25

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:24:

GCGAAGCTTG AAAGCCCTCA GGAGG                                     25

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:25:

GCGAAGCTTA AACAGGCTCC AGAAG                                     25

(2) INFORMATION FOR SEQ ID NO:26:

(i) SEQUENCE CHARACTERISTICS:
        (A) LENGTH: 19 base pairs
        (B) TYPE: nucleic acid
```

```
            (C) STRANDEDNESS: single
            (D) TOPOLOGY: linear (xi) SEQUENCE DESCRIPTION: SEQ ID NO:26:

GATGTACAGT GGGCTAAGC                                                19

(2) INFORMATION FOR SEQ ID NO:27:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:27:

GCGAAGCTTG GAAGGGAGAG AGGTTGC                                       27

(2) INFORMATION FOR SEQ ID NO:28:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:28:

GCGAAGCTTG ATGCCAAAGG AATAC                                         25

(2) INFORMATION FOR SEQ ID NO:29:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:29:

GCGAAGCTTG TCTGGAACTG CATCC                                         25

(2) INFORMATION FOR SEQ ID NO:30:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:30:

GCGAAGCTTC TAAACTACCT AAGAG                                         25

(2) INFORMATION FOR SEQ ID NO:31:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:31:

GCGAAGCTTG TGACTTTGAA CAGTG                                         25

(2) INFORMATION FOR SEQ ID NO:32:

(i) SEQUENCE CHARACTERISTICS:
            (A) LENGTH: 25 base pairs
            (B) TYPE: nucleic acid
            (C) STRANDEDNESS: single
            (D) TOPOLOGY: linear
```

(xi) SEQUENCE DESCRIPTION: SEQ ID NO:32:

GCGAAGCTTT TTAAAGAAAA TTGGC                                      25

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:33:

GCGAAGCTTG GGCTATGCGA TTTGGC                                     26

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:34:

GCGAAGCTTC TTTCTCTGAG TGACTCC                                    27

(2) INFORMATION FOR SEQ ID NO:35:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GTCTGGAACT GCATCCAAAT TCAGGTTCAG TAATGATGGC ATTATCCAAA            50

(2) INFORMATION FOR SEQ ID NO:36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:36:

AGTAATGATG TCATTATCCA AA                                         22

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:37:

AGTAATGATT CATTATCCAA A                                          21

(2) INFORMATION FOR SEQ ID NO:38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:38:

AGTAATGATG TGTCATTATC CAAA                            24